United States Patent [19]
Cartmell et al.

[11] Patent Number: 5,478,308
[45] Date of Patent: Dec. 26, 1995

[54] WOUND PACKING AND PACKAGE THEREFOR

[75] Inventors: James V. Cartmell, Xenia; Wayne R. Sturtevant, Centerville; Michael L. Wolf, West Milton, all of Ohio

[73] Assignee: New Dimensions in Medicine, Inc., Dayton, Ohio

[21] Appl. No.: 300,745

[22] Filed: Sep. 6, 1994

Related U.S. Application Data

[63] Continuation-in-part of Ser. No. 862,456, Apr. 2, 1992, Pat. No. 5,429,589, and a continuation-in-part of Ser. No. 144,003, Nov. 1, 1993.

[51] Int. Cl.⁶ ................................................. A61F 13/36
[52] U.S. Cl. ............................. 602/57; 602/42; 604/13
[58] Field of Search .......................... 602/3, 41, 42–46, 602/48, 49, 52, 54, 56, 57, 58, 60, 75; 604/11, 13, 27, 57, 60, 304, 309, 367, 368, 904; 206/438, 440, 441

[56] References Cited

U.S. PATENT DOCUMENTS

| | | | |
|---|---|---|---|
| 2,682,873 | 7/1954 | Evans et al. | 602/42 |
| 4,281,650 | 8/1981 | Spiegelberg | 128/156 |
| 4,717,378 | 1/1988 | Perrault et al. | |
| 4,838,885 | 6/1989 | Bernardin | |
| 4,842,593 | 6/1989 | Jordan et al. | |
| 4,842,597 | 6/1989 | Brook | |
| 4,848,329 | 7/1989 | Dardik | |
| 4,865,596 | 9/1989 | Weisman et al. | |
| 4,909,244 | 3/1990 | Quarfoot et al. | |
| 4,930,500 | 6/1990 | Morgan | |
| 4,983,773 | 1/1991 | Patience et al. | |
| 4,984,570 | 1/1991 | Langen et al. | |
| 5,059,424 | 10/1991 | Cartmell et al. | |
| 5,061,259 | 10/1991 | Goldman et al. | |
| 5,087,242 | 2/1992 | Petelenz et al. | |
| 5,112,618 | 5/1992 | Cartmell et al. | |
| 5,115,801 | 5/1992 | Cartmell et al. | |
| 5,135,472 | 8/1992 | Hermann et al. | |
| 5,254,109 | 10/1993 | Smith et al. | 604/289 |

*Primary Examiner*—C. Fred Rosenbaum
*Assistant Examiner*—Bryan L. Tsosie
*Attorney, Agent, or Firm*—Killworth, Gottman, Hagan & Schaeff

[57] ABSTRACT

A sterile wound packing material and package therefor is provided, which wound packing is flexible and conformable to deep and/or irregular shaped wounds, is compact and easily dispensed, and which can be stored indefinitely. The wound packing may also be used for absorbing wound exudate and immediately discarded or by be designed to remain in place for extended periods during healing. The wound packing includes a sterile, wound packing of a flexible material capable of absorbing wound exudate, with the flexible material being in the form of a substantially flat, coiled, spirally-cut layer and a package therefor. In certain embodiments of the invention where it is desired that the wound packing remain in place for an extended period, the flexible material is impregnated with a hydrogel, which may be a "wet" hydrogel (i.e., one containing substantial amounts of water) or a dehydrated hydrogel which is substantially devoid of water but becomes hydrated in use.

14 Claims, 5 Drawing Sheets

WOUND PACKING AND PACKAGE THEREFOR

CROSS REFERENCE TO RELATED APPLICATIONS

This application is a continuation-in-part of U.S. application Ser. No. 07/862,456, filed Apr. 2, 1992, now U.S. Pat. No. 5,429,589, entitled HYDROGEL GAUZE WOUND DRESSING and of U.S. application Ser. No. 08/144,003, filed Nov. 1, 1993, entitled WOUND PACKING AND PACKAGE THEREFOR. This application is also related to U.S. application Ser. No. 07/921,916, filed Jul. 29, 1992, and entitled HYDROGEL GAUZE, now abandoned, which is a continuation-in-part of application Ser. No. 07/862,456 and application Ser. No. 08/082,806, filed Jun. 25, 1993, and entitled HYDROGEL GAUZE, which is a continuation of application Ser. No. 07/921,916.

BACKGROUND OF THE INVENTION

The present invention relates to a sterile wound packing and a package therefor, and, more particularly to a wound packing in the form of a flexible spirally-cut layer capable of absorbing wound exudate and to a package for dispensing the wound packing.

Secreting skin wounds, such as decubitus ulcers and open surgical wounds, have long presented a medical challenge in keeping such wounds sterile and relatively dry. Deep wounds provide an even greater challenge. The accumulation of wound exudate, such as blood, pustulation, and other wound fluids, in wound crevices, promotes growth of bacteria and other organisms which cause infection and delay the healing process. Such wound exudate may also cause maceration of tissue adjacent the would and support infection thereof.

However, since it is often desirable to allow a wound to heal in a slightly "moist" or occlusive state, which is believed to accelerate healing excess wound exudate must be removed. If excess wound exudate remains in or on a wound, a "blister" of exudate can form under the wound dressing which is not only unsightly, but also may cause the dressing to leak, thereby defeating the aim of sterility. However, existing methods of aspiration can lead to wound infection or can destroy sterility. Additionally, it is not desirable to remove all the exudate as that would result in a "dry" wound resulting in a slower healing process.

There is a substantial body of prior art relating to wound and/or surgical dressings or packings for treating skin lesions, such as decubitus ulcers and open wounds. In some instances, the wound dressing or packing may be designed to be only temporary, such as the use of gauze to absorb blood and/or other wound exudate. In others, the wound dressing is designed to be more permanent in nature, remaining in place for several hours or days during the healing process. In yet other instances, the wound dressing material is designed to be biodegradable and to break down over an extended period of time as a wound heals.

Aqueous moisture absorbing materials, such as a hydrogel material with a polyethylene glycol liquid curing agent, as disclosed in Spence, U.S. Pat. No. 4,226,232, have been used as dressings on a wound site, but cannot be sterilized by irradiation due to the formation of free radicals within the aqueous material. Another aqueous absorbing material used to absorb wound exudate is a hydrophilic polymer as disclosed in Rawlings et al, U.S. Pat. No. 4,657,006. Rawlings et al disclose a wound dressing which comprises a hydrophilic polymer having moisture and vapor permeability characteristics. However, a problem with the Rawlings et al wound dressing is that the wound exudate absorbed by the hydrophilic polymer hardens or solidifies the polymer, allowing pockets to develop between the polymer and the wound, thereby providing an excellent environment for bacteria proliferation.

In addition, wound dressings used in the past have not been conducive for healing extremely deep wounds and wounds having irregular shapes. To that end, wound dressings and surgical sponges formed from gauze and foam materials have been used for many years surgical practice. These sponges and wound dressings have attempted to retain both the advantages of thin, soft and flexible single layer dressings and the absorptive cushioning and insulating properties of thicker pad-like structures. As a result, the sponges and wound dressings have traditionally been formed of multiple layers of thin, soft, low count gauze material which are unified along fairly widely separated lines usually extending longitudinally or transversely.

Although such wound dressings and surgical sponges have been found useful in the past, none have provided the capability of absorbing large amounts of wound exudate without inhibiting the healing of the wound to which they are contacted. Most all of these dressings, including gauze and sponges, adhere to the wound upon removal, thereby damaging the wounds to which they are attached. This in turn prolongs the healing of such wounds. It would therefore be desirable to have a wound dressing or packing having a structure which is thin, flexible and soft yet absorbs wound exudate in the same manner as the more thick pad-like wound dressings.

Another problem with prior wound dressings or packings is the need to maintain their sterile condition both prior use and during application to a wound. To maintain sterility, the wound dressings are packaged in metal foil or metallized plastic containers. Aqueous hydrogel wound dressings require moisture barrier packaging to prevent them from drying out during storage prior to use. In many instances, the packaging used for such products represents a significant additional cost over and above the cost of the wound dressing itself and/or is difficult for an end user to open or dispense the wound dressing.

Accordingly, there is a need in the art for a wound packing which is especially conducive for wounds which penetrate the surface of the skin. There is also a need for such a wound packing which has a thin, flexible and soft structure so as to permit the wound packing to be sterilized and readily available for application to a draining wound having irregular shapes and depths. Finally, there is a need for such a wound dressing which can be conveniently packaged and dispensed while maintaining its sterility.

SUMMARY OF THE INVENTION

The present invention meets those needs by providing a sterile wound packing material and package therefor which wound packing is flexible and conformable to deep and/or irregular shaped wounds, is compact and easily dispensed, and which can be stored indefinitely. The wound packing of the present invention may also be designed to be used for absorbing wound exudate and immediately discarded or may be designed to remain in place for extended periods during healing.

According to one aspect of the present invention, a sterile wound packing is provided and includes a sterile, wound packing and a package therefor. The wound packing includes a flexible wound packing material capable of absorbing wound exudate, with the wound packing material being in the form of a substantially flat, coiled, spirally cut layer. The wound packing material is selected from the group consisting of woven gauze, fabric, nonwoven natural or synthetic fibers, polymeric sheets and films, and the like. In certain embodiments of the invention where it is desired that the wound packing remain in place for an extended period, the wound packing material is impregnated with a hydrogel, which may be a "wet" hydrogel (i.e., one containing substantial amounts of water) or a dehydrated hydrogel which is substantially devoid of water but becomes hydrated in use.

The package for the wound packing material includes sealed first and second sheets with the flexible wound packing material therebetween. The first and second sheets are made of any suitable material capable of maintaining the sterility of the contents of the package such as metal foil, metal-coated polymer, polymer, paper, or coated paper. The package is preferably opened by peeling apart the first and second sealed sheets. Preferably, a portion of the package is sealed such that a free-lifting edge or corner is provided to facilitate peeling apart the sheets. The spirally-cut packing may then be removed by pulling on one end thereof. The wound packing may be cut to length as needed or may be designed to be packaged in different widths and lengths.

The package also includes a backing layer adhered to a portion of the inner surface of one of the first and second sheets, with the wound packing material positioned on the backing layer. Preferably, the backing layer comprises a polymer such as polyester which includes a release coating on its surface. The wound packing material is positioned on the backing layer such that it contacts the release coating. The backing layer prevents the wound packing material from shifting inside the unopened package, and, once the package has been opened, supports the packing while it is being dispensed.

The package also preferably includes means for protecting the wound packing material from contamination prior to dispensing it from the opened package. The protecting means may comprise a release liner or card stock which overlies the wound packing material inside the package.

Accordingly, it is a feature of the present invention to provide a wound packing which is flexible and conformable deep and/or irregular shaped wounds, and to provide a package which allows the wound packing to be easily dispensed and stored indefinitely in a compact, sterile condition. It is another feature of the present invention that the wound packing may also be designed to be used for absorbing wound exudate and then immediately discarded or may be designed to remain in place for extended periods during healing. These, and other features and advantages of the present invention will become apparent from the following detailed description, the accompanying drawings, and the appended claims.

DETAILED DESCRIPTION OF THE PREFERRED EMBODIMENTS

Figure 1:
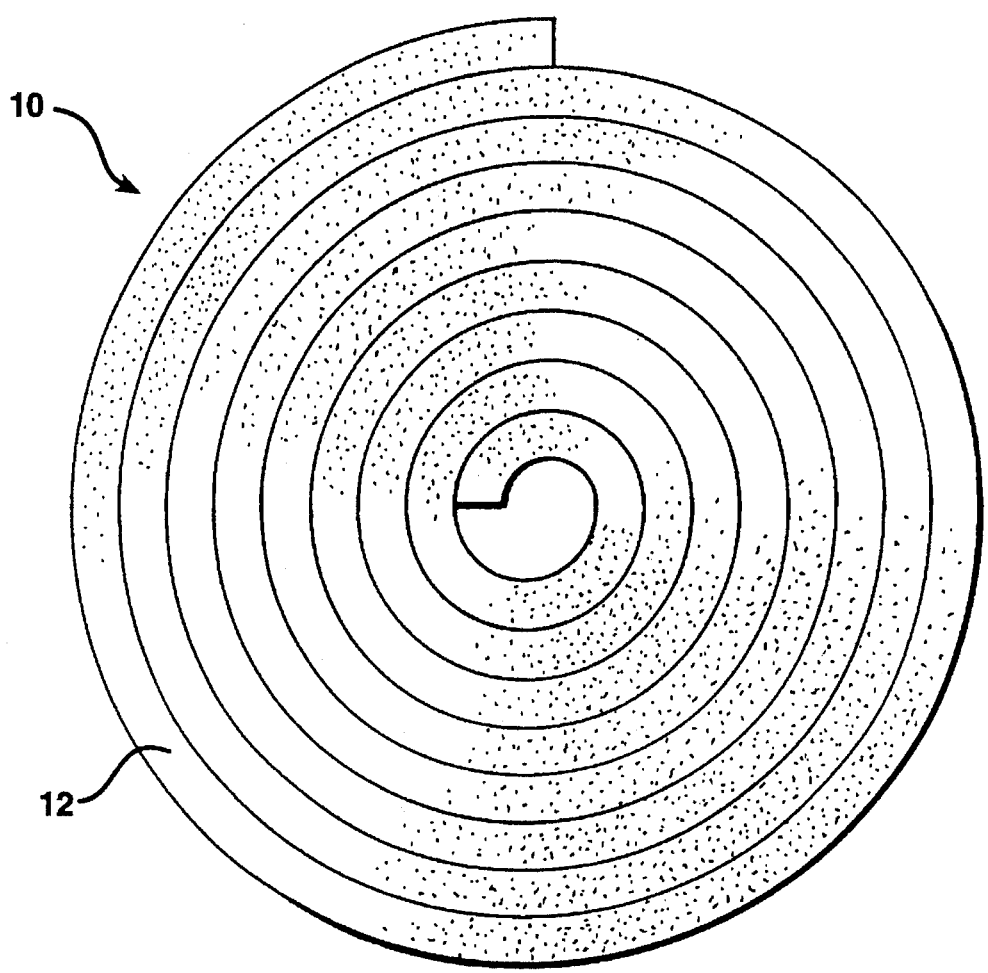
FIG. 1 is a top view of the wound packing illustrating the spiral-cut configuration.

The present invention provides a sterile wound packing 10 in the form of a thin, flexible absorbent structure suitable for use in the treatment of wounds on a patient. As shown in FIG. 1, the wound packing 10 comprises a flexible absorbent layer 12 which may optionally have a dehydrated or hydrated hydrogel material impregnated therein for absorbing wound exudate. While those skilled in the art will appreciate the difficulty in illustrating the presence of a hydrogel material in absorbent layer 12, it should be understood that the optional hydrogel material when used is preferably completely impregnated in the interstices between fibers of the absorbent layer 12.

It is preferred that the absorbent layer 12 be formed of material which is capable of absorbing wound exudate and or blood cells, as well as being capable of supporting the optional hydrogel material. Those skilled in the art will appreciate that materials having interstices within which materials may be absorbed or impregnated are particularly suitable for such purposes. Examples of suitable materials for absorbent layer 12 include woven gauze, natural or synthetic fabrics, nonwoven natural or synthetic fibers (e.g., felts), or polymeric sheets and films to the extent that they can be fabricated to include interstices and be absorbent. Absorbent layer 12 can comprise a single fibrous layer, a plurality of layers stacked one atop the other, or a felt-like nonwoven material. Typically, the material of absorbent layer 12 will have a thickness of from several mils to a few hundred mils (about $7.62 \times 10^{-3}$ cm to 0.76 cm).

As shown, wound packing 10 is in the form of a substantially flat, coiled spiral-cut layer of material. As explained in greater detail below, the material may be manufactured in the form of a continuous web which can then optionally be impregnated with a hydrogel and cut into desired sizes. For example, an approximately 5 inch diameter disk of absorbent material may be spiral cut into a continuous ¼ inch width strip to provide over six feet of wound packing. Similarly an approximately 8 inch diameter disk of absorbent material may be spiral cut into a continuous 1 inch width strip to provide over three feet of wound packing. Those skilled in this art will recognize that there are many combinations of widths and lengths of the wound packing material which can be manufactured. Because of the spiral cut design, the wound packing may be easily packaged compactly and in a variety of widths and lengths.

Figure 2:
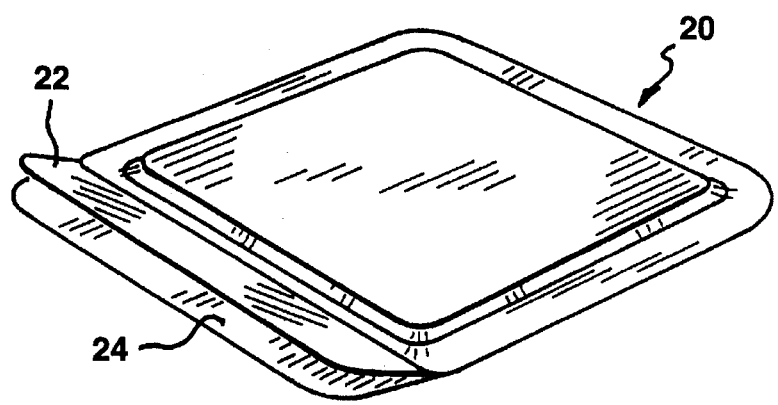
FIG. 2 is a perspective view of a sealed package containing the wound packing with a free-lifting edge for peeling.

Referring now to FIG. 2, a package 20 is provided for the wound packing. Package 20 includes peripherally sealed first and second sheets 22, 24 which contain wound packing 10 (not shown) therebetween. First and second sheets 22, 24 may be made from any suitable material capable of maintaining the sterility of the wound packing 10 within the package. Examples of suitable sheet material include metal foils, metal coated polymer sheets, polymers (including but not limited to those which provide moisture and/or gas barrier properties), paper, or coated paper. Where an optional hydrated hydrogel is impregnated into the wound packing, it is preferred that packaging with moisture barrier properties be used to insure a long shelf life for the package.

The sheets may be heat sealed together or adhesively sealed, such as by a bead of peripheral adhesive 26 (shown in FIG. 3) on one or both sheets. Alternatively, any sealing process which results in an air-tight seal to maintain the sterility of the wound packing within the package is suitable. As shown in FIG. 2, one side portion of the perimeter of the package is sealed so that the edges of the two sheets are free-lifting and may be peeled apart. It will be appreciated that other variations of this embodiment may also be employed. For example, the package can be configured so that the sheets include a free-lifting corner section of the package. If desired, a tab may be included between the two sheets along an edge or in a corner to facilitate grasping and peeling apart of the sheets. The package may also include a cut or notch along an edge which will facilitate tearing for opening of the package.

Figure 3:
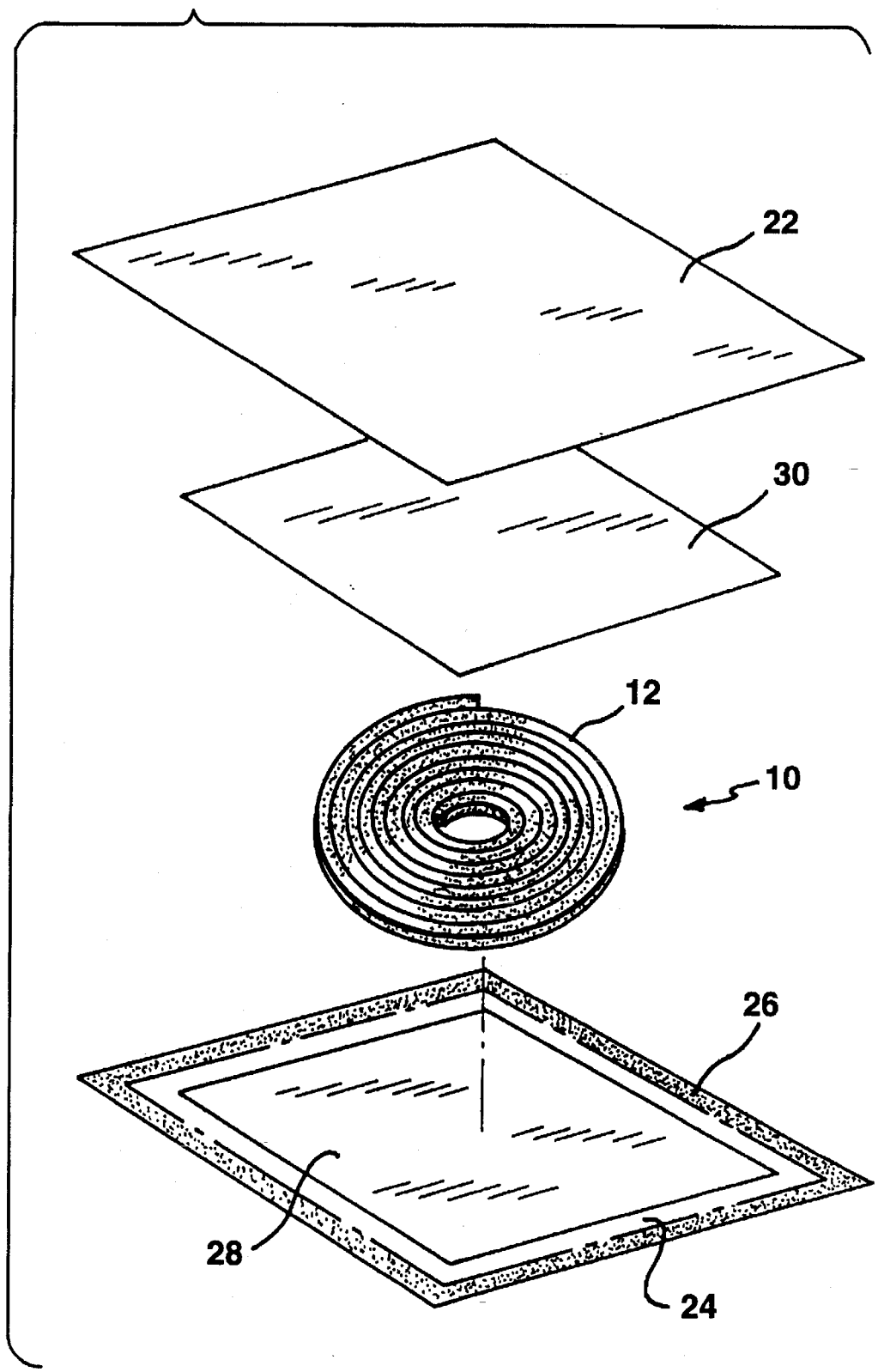
FIG. 3 is an exploded perspective view of the wound packing and package of FIG. 2, including a backing layer and a release layer.

Referring now to FIG. 3, the wound packing and package are shown in exploded view. The package includes a backing layer 28 which is adhered to the inner surface of sheet 24. The backing layer preferably comprises a polymer such as polyester or polyethylene although other suitable materials such as paper may be used. Polyester is the preferred backing layer for the present invention as it is a strong film which is easy to kiss-cut for manufacturing purposes as will be explained in greater detail below. The backing layer is coated on its surface with a release coating such as silicone, and is coated on its opposite surface with a pressure sensitive adhesive which adheres to the inner surface of sheet 24. The wound packing 10 is positioned on the backing layer 28 such that it contacts the release coating. Once adhered to the inside of the package, the backing layer supports the wound packing in position until it is dispensed.

The package also preferably includes means for protecting the wound packing from contamination prior to dispensing which comprises a release liner 30. The release liner preferably comprises polyethylene and may include a release coating on the side of the liner which contacts wound packing 10. Card stock, preferably coated, may also be used as an alternative means of protection.

Figure 4:
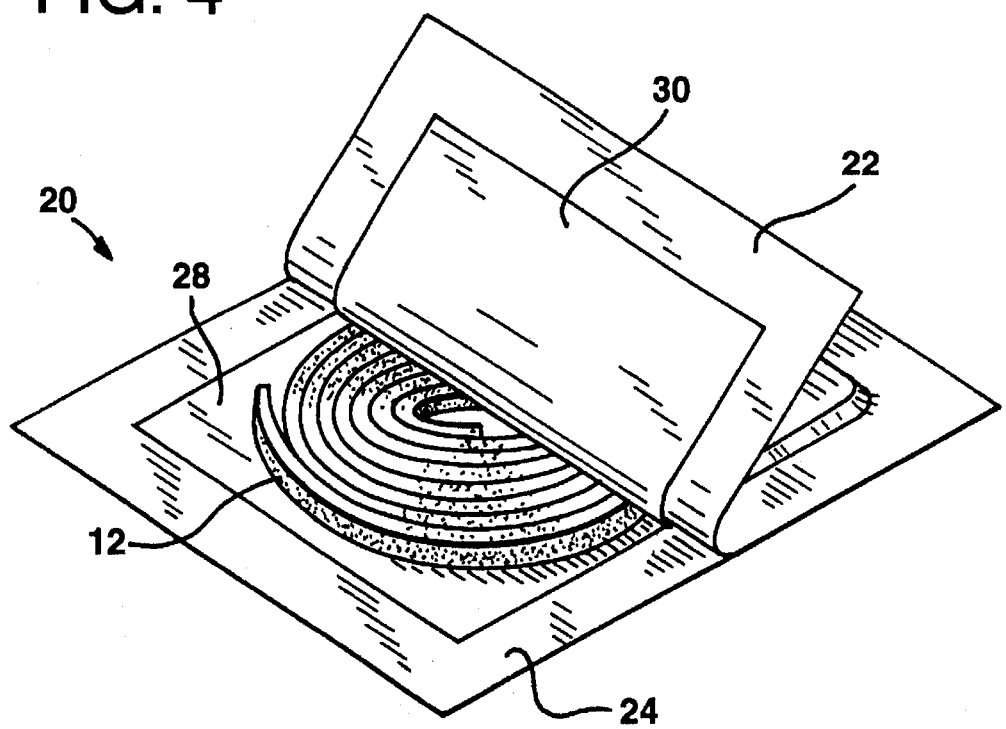
FIG. 4 is a perspective view of a package containing a spiral cut wound packing being peeled away from the polyester backing layer of the packaging.

Referring now to FIG. 4, once the first and second sheets 22 and 24 have been peeled apart, and release liner 30 has been peeled away from the wound packing, an end of absorbent material 12 may be peeled away from the backing layer 28 to a desired length or amount. The absorbent material 12 may then be cut. Alternatively, the entire contents of package 20 may be removed and used at the same time.

Figure 5:
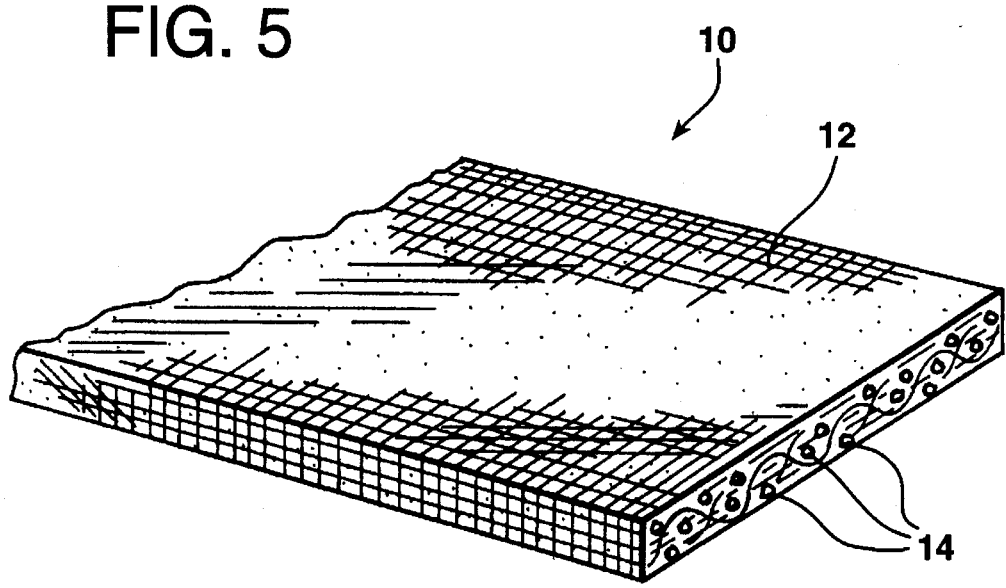
FIG. 5 is an enlarged, partially cut away perspective of one embodiment of the wound packing of the present invention.

While it is within the scope of the invention for absorbent layer 12 to contain no coatings or impregnants (for example, sterile woven gauze is a useful wound packing material), it may be desirable to include in absorbent layer 12 a hydrogel material which may be hydrated or dehydrated. FIG. 5 illustrates (in a greatly enlarged view for purposes of illustration) one embodiment of the invention in which wound packing 10 (prior to being cut into its spiral 35 configuration) comprises an absorbent layer 12 having dehydrated hydrogel material 14 impregnated therein for absorbing wound exudate. It is preferable that dehydrated hydrogel material 14 is completely impregnated in the interstices between fibers of the absorbent layer 12. It is also preferable to have dehydrated hydrogel material 14 completely impregnated in the interstices of absorbent layer 12 such that dehydrated hydrogel material 14 is substantially exposed at the outer surfaces of wound packing 10 so that absorbent layer 12 is precluded from adhering to the patient's wound. Further, dehydrated hydrogel material 14 must be able to adhere to the absorbent layer 12 so as to form a flexible, thin, structure which, when contacted with a draining wound on a patient, absorbs large amounts of wound exudate without inhibiting the healing of such wound. In this manner, wound packing 10 can be removed from the wound to which it is adhered in a non-destructive manner such that it does not adhere to the new cell tissue forming in the healing wound. Wound dressing 10 also does not break apart into fragments or lumps, but rather, can be removed substantially as a single piece because of its woven or intertwined fibrous composition. Such features have not been present in past thin, flexible, gauze-type wound dressings. These features are largely attributed to the hydrogel material from which dehydrated hydrogel material 14 is formed. These materials are discussed more fully below.

Figure 6:
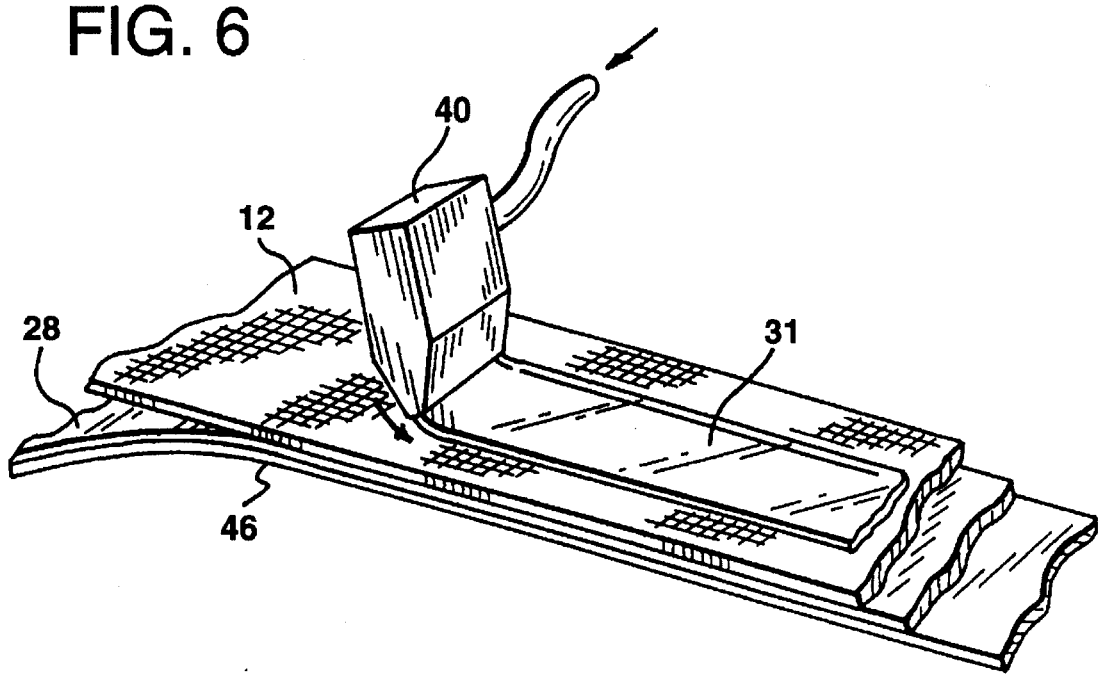
FIGS. 6 and 6A are schematic views illustrating a process by which the wound packing and package can be made.
Figure 6A:
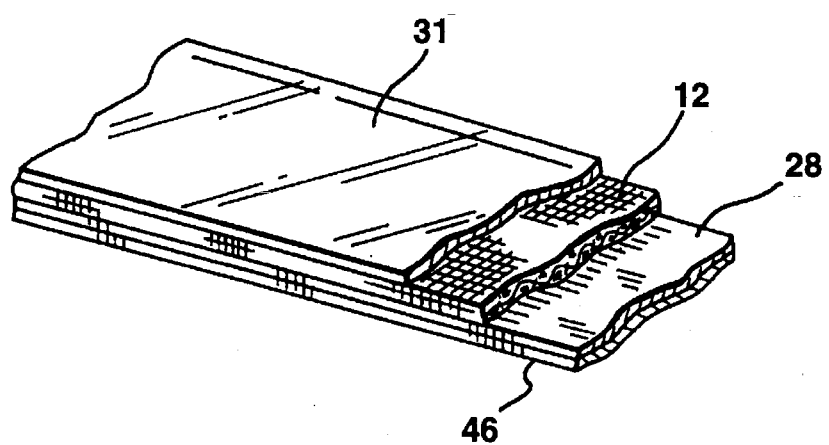

For purposes of providing a more intuitive understanding of the wound packing 10 and package 20, a process by which the wound packing 10 and package can be made is schematically illustrated in FIGS. 6 and 6A. As seen in FIG. 6, a backing sheet 28, preferably with a release coating on its surface, is advanced on a feed line. The sheet 28 has a pressure sensitive adhesive on its opposite surface which is covered with a release liner 46.

An absorbent layer 12 is also fed in continuous web form onto the feed line so that the web is in contact with the release coated surface of the backing sheet 28, such as, for example, a silicone coated polyester.. The absorbent layer 12 is fed under an applicator 40 capable of receiving and applying a liquid or uncured hydrogel material 42 from a source (not shown) without permitting it to cure within its components. Applicator 40 applies uncured hydrogel material 42 onto absorbent layer 12 in an amount sufficient to impregnate the interstices therein and provide exposure of the hydrogel at the outer surfaces of layer 12. As those skilled in the art will appreciate, the amount of uncured hydrogel material 42 applied will vary with the particular material used as absorbent layer 12 and the width and thickness of the web to be coated.

Figure 8:
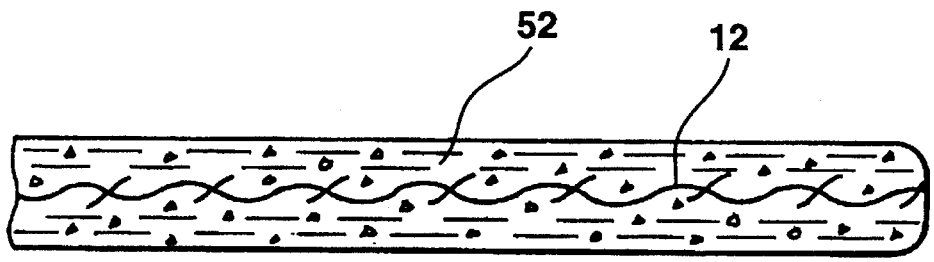
FIG. 8 is a cross-sectional view of the wound packing of FIG. 7.

Uncured hydrogel material 42 is then allowed to cure downstream on the feed line to form a hydrated hydrogel material 52 surrounding and impregnating absorbent layer 12 (FIG. 8). Once the absorbent layer has been impregnated with hydrogel, a release coated polymer film 31 is laminated to the top of the hydrogel-impregnated absorbent layer 12 such that the absorbent layer is sandwiched between sheets 31 and 28 as shown in FIG. 6A.

Thereafter, the continuous web of wound packing 10 may be cut into individual sheets. The wound packing is then spiral cut to the form shown in FIG. 1. Spiral cutting is accomplished using a kiss-cut die, where the die cuts through the release-coated film 3i and the hydrogel impregnated absorbent layer 12, but not the backing sheet 28. After cutting, film 31 is then removed, and a fresh sheet of a release-coated material such as silicone coated polyethylene is laminated to the spiral-cut wound packing. This sheet of polyethylene remains on the wound packing as release liner 30.

The polyethylene and polyester sheets are then die cut so that both sheets extend beyond the edges of the wound packing. The release liner 46 is then removed from the adhesive coated surface of backing layer 28. The backing layer 28 may then be adhered to the inner surface of one of the sheets of the package, with the spiral cut wound dressing sandwiched between the backing layer 28 and the release liner 30. The first and second sheets of the package are then adhered together to form a sealed package 20 as shown in FIG. 2.

The hydrogel may be in a hydrated or dehydrated condition. If it is desired to dehydrate the hydrogel, wound packing 10 is first dried, oven-baked or otherwise dehydrated so as to substantially completely evaporate the water contained in the hydrogel material 52 which was applied onto absorbent layer 12. The result is a finished, flexible, and sterile wound packing 10 sealed in package 20.

Figure 7:
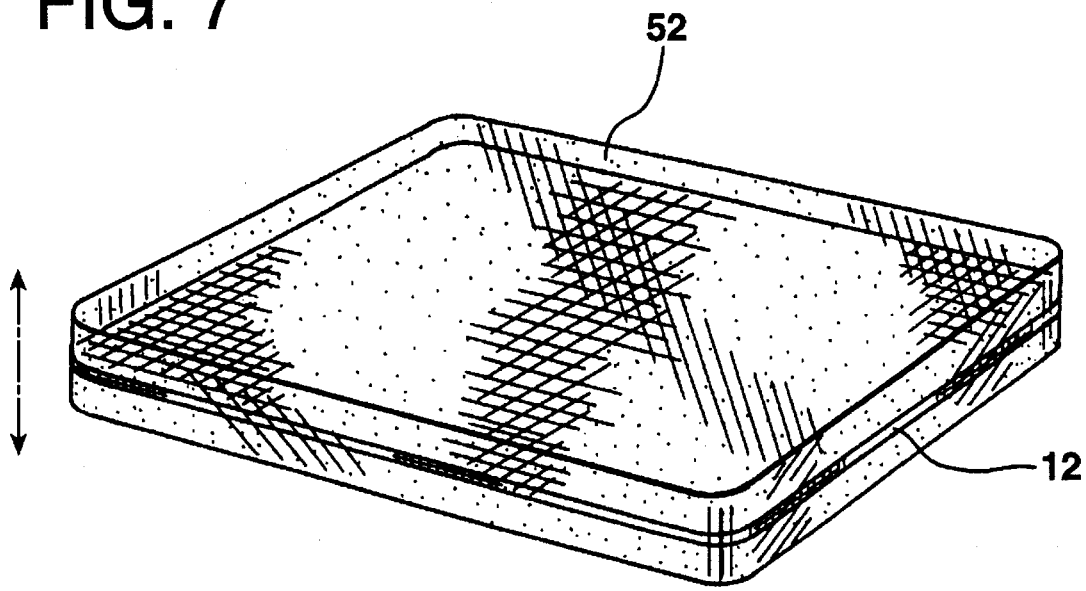
FIG. 7 illustrates one embodiment of the wound packing after it has been applied to a draining wound.

Referring now to FIG. 7, which has been greatly enlarged for purposes of illustration, a small piece of wound packing 10, after having been contacted with a draining wound, is illustrated. Where a dehydrated hydrogel has been used, FIG. 7 illustrates the expansion or swelling (as depicted by the arrows in dotted lines) of the dehydrated hydrogel material 14 upon acquisition of bodily fluids, such as wound exudate, from the wound to which the wound packing 10 is applied. The expanded or hydrated hydrogel material is referred to herein by reference numeral 52. Wound dressing 10, when it contains optional dehydrated hydrogel 14, is therefore analogous to a sponge in that its initial dehydrated state expands as fluids are absorbed.

FIG. 8 may also be considered to illustrate a cross-sectional view of a small piece of wound dressing 10 depicted in FIG. 7 and shows hydrogel material 52 swelled in and around absorbent layer 12. As those skilled in the art will appreciate, hydrogel material 52 depicted in FIG. 7 is the same as the cured hydrogel material 52 discussed with respect to the process by which wound packing 10 is made and illustrated in FIG. 6. In essence, cured and hydrated hydrogel material 52 may be initially dehydrated for packaging and then returned to its original hydrated state upon wound exudate absorption.

The preferred hydrogel material for use in the present invention is formed from an aqueous mixture of polyhydric alcohol, an aliphatic diisocyanate terminated prepolymer, polyethylene oxide based diamine and sodium chloride. Preferably, the polyhydric alcohol is selected from the group consisting of polypropylene glycol, polyethylene glycol and glycerine. The hydrogel material 52 in its dehydrated state, which is referred to herein as the dehydrated hydrogel material 14, provides a highly absorbent material capable of retaining large amounts of wound exudate, thereby rendering it very suitable for use in wound packings. By forming the hydrogel material 52 from the aforementioned aqueous mixture, wound packing 10 remains intact as it absorbs wound exudate from the wound.

Moreover, the preferred hydrogel material does not adhere or stick to the wound thereby allowing for easy removal of wound packing 10 substantially as a single piece. Additionally, the biocompatibility of the hydrogel material within the wound is extremely favorable. Thus, the resulting hydrogel material 52, and therefore the dehydrated hydrogel material 14, provides a bio-compatible, non-irritating, fluid absorbing, bacterial protective, cushioning, skin-like media over the wound site. An additional advantage of the hydrogel material 52 is that it may be transparent, rendering it possible to inspect the wound site through absorbent layer 12 without removing wound packing 10 for those embodiments where the openings between fibers in layers 12 are sufficient to permit viewing.

The preferred aliphatic diisocyanate terminated prepolymer is an isophorone diisocyanate terminated prepolymer based on polyols containing more than about 40% polyethylene oxide and having an isocyanate content of about 3% by weight. The molecular weight of the isophorone diisocyanate terminated pro, polymer is preferably in a range from about 1500 to about 8000 and most preferably, from about 4000 to about 5000. The polyethylene oxide based polyamine is preferably a polyethylene oxide based diamine having a molecular weight in a range from about 200 to about 6000 and most preferably, about 2000. It is also preferable that the aliphatic diisocyanate terminated prepolymer and the polyethylene oxide based polyamine have a stoichiometric ratio of about 1:1. Those skilled in the art will appreciate that all of the constituents with the preferred hydrogel material may be readily synthesized or purchased commercially neither of which is more preferred.

It has been found that more preferred hydrogel material 52, and therefore the dehydrated hydrogel material 14, is formed from an aqueous mixture including from about 0% to about 90% by weight polyhydric alcohol; from about 6% to about 60% by weight aliphatic diisocyanate terminated prepolymer; from about 4% to about 40% by weight polyethylene oxide based polyamine; up to about 2% by weight sodium chloride; and the balance water. A more preferred hydrogel composition for forming the hydrogel material 30 is formed from a mixture comprising from about 15% to about 30% by weight polypropylene glycol; from about 8% to about 14% by weight isophorone diisocyanate terminated prepolymer; from about 5% to about 10% by weight polyethylene oxide based diamine; and up to about 1% by weight sodium chloride; and the balance water. Most preferably, the hydrogel material 30 is formed from a mixture comprising: (a) from about 16% to 17% by weight polypropylene glycol; (b) from about 10% to 12% by weight isophorone diisocyanate terminated prepolymer; (c) from about 7% to 9% by weight polyethylene oxide based diamine; (d) about 0.58% to 1% by weight sodium chloride; and (e) the balance water.

The aforementioned preferred hydrogel compositions provide a wound packing 10 having the desired properties of excellent biocompatibility and absorption of exudate properties without adhering to the wound. However, other materials having such characteristics, including but not limited to the aforementioned hydrogel compositions, may be used to form the hydrogel material 52 in accordance with the present invention.

While certain representative embodiments and details have been shown for purposes of illustrating the invention, it will be apparent to those skilled in the art that various changes in the methods and apparatus disclosed herein may be made without departing from the scope of the invention, which is defined in the appended claims.

What is claimed is:

1. A sterile wound packing comprising:
   a flexible wound packing material capable of absorbing wound exudate, said wound packing material in the form of a substantially flat, coiled, spirally-cut layer; and
   a package for said wound packing material, said package comprising a first sheet and a second sheet having inner and outer surfaces, said first sheet and said second sheet sealed together with said wound packing material therebetween, said package including a backing layer adhered to said inner surface of one of said first and second sheets, wherein said wound packing material is positioned on said backing layer.

2. The sterile wound packing of claim 1 wherein said backing layer comprises polyester.

3. The sterile wound packing of claim 2 wherein said backing layer includes first and second surfaces and said first surface of said polyester backing layer includes a release coating and wherein said wound packing material contacts said release coating.

4. The sterile wound packing of claim 1 including means for protecting said wound packing material from contamination.

5. The sterile wound packing of claim 1 including means for facilitating opening of said package.

6. The sterile wound packing of claim 5 in which said package is sealed such that a free-lifting edge is provided to facilitate peeling apart said first and second sheets.

7. The sterile wound packing of claim 1 in which said wound packing material is selected from the group consisting of woven gauze, fabric, nonwoven natural or synthetic fibers, polymeric sheets and films.

8. The sterile wound packing of claim 7 in which said wound packing material is impregnated with a hydrogel.

9. The sterile wound packing of claim 7 in which said wound packing material is impregnated with a hydrocolloid.

10. The sterile wound packing of claim 7 in which said wound packing material is impregnated with a medicament.

11. The sterile wound packing of claim 1 in which said first and second sheets of said package are comprised of materials selected from the group consisting of metal foil, metal-coated polymer, polymer, paper, and coated paper.

12. A sterile wound packing comprising:

a flexible wound packing material capable of absorbing wound exudate, said wound packing material in the form of a substantially flat, coiled, spirally-cut layer;

card stock for protecting said wound packing material from contamination; and a package for said wound packing material, said package comprising a first sheet and a second sheet having inner and outer surfaces, said first sheet and said second sheet sealed together with said wound packing material therebetween, said package including a backing layer adhered to said inner surface of one of said first and second sheets, wherein said wound packing material is positioned on said backing layer.

13. A sterile wound packing comprising:

a flexible wound packing material capable of absorbing wound exudate, said wound packing material in the form of a substantially flat, coiled, spirally-cut layer;

a release liner on said wound packing material for protecting said wound packing material from contamination; and a package for said wound packing material, said package comprising a first sheet and a second sheet having inner and outer surfaces, said first sheet and said second sheet sealed together with said wound packing material therebetween, said package including a backing layer adhered to said inner surface of one of said first and second sheets, wherein said wound packing material is positioned on said backing layer.

14. A sterile wound packing comprising:

a flexible wound packing material capable of absorbing wound exudate, said wound packing material in the form of a substantially flat, coiled, spirally-cut layer, wherein said wound packing material is impregnated with a dehydrated hydrogel which is substantially devoid of water; and a package for said wound packing material, said package comprising a first sheet and a second sheet having inner and outer surfaces, said first sheet and said second sheet sealed together with said wound packing material therebetween, said package including a backing layer adhered to said inner surface of one of said first and second sheets, wherein said wound packing material is positioned on said backing layer.

* * * * *